US012505973B2

(12) United States Patent
Ziskin et al.

(10) Patent No.: US 12,505,973 B2
(45) Date of Patent: Dec. 23, 2025

(54) COMPACT X-RAY ELECTRON BEAM SCAN TUBE, SYSTEM AND METHOD

(71) Applicant: NAUTILUS XRAY, INC., Las Vegas, NV (US)

(72) Inventors: Vitaliy Ziskin, Las Vegas, NV (US); Hong Chen, Las Vegas, NV (US); Andrew G. Cross, Las Vegas, NV (US); Hui Hu, Las Vegas, NV (US)

(73) Assignee: NAUTILUS XRAY INC., Las Vegas, NV (US)

( * ) Notice: Subject to any disclaimer, the term of this patent is extended or adjusted under 35 U.S.C. 154(b) by 192 days.

(21) Appl. No.: 18/321,633

(22) Filed: May 22, 2023

(65) Prior Publication Data

US 2024/0395491 A1 Nov. 28, 2024

(51) Int. Cl.

| | |
|---|---|
| ***H01J 35/14*** | (2006.01) |
| ***A61B 6/40*** | (2024.01) |
| ***H01J 35/08*** | (2006.01) |
| ***H01J 35/30*** | (2006.01) |
| ***H05G 1/52*** | (2006.01) |

(52) U.S. Cl.

CPC .......... *H01J 35/153* (2019.05); *A61B 6/4021* (2013.01); *H01J 35/112* (2019.05); *H01J 35/30* (2013.01); *H05G 1/52* (2013.01); *A61B 6/4028* (2013.01)

(58) Field of Classification Search

CPC ........ H01J 35/153; H01J 35/30; A61B 6/4021

See application file for complete search history.

(56) References Cited

U.S. PATENT DOCUMENTS 4,352,021 A 9/1982 Boyd et al.
5,172,401 A * 12/1992 Asari ........................ H05G 1/70 378/10
5,247,556 A * 9/1993 Eckert .................. A61B 6/4028 378/98.2

(Continued)

FOREIGN PATENT DOCUMENTS

EP 127983 A * 12/1984 ............. A61B 6/032
JP S6012656 A 1/1985

OTHER PUBLICATIONS

International Search Report from Corresp. PCT Appln. No. PCT/US2024/029701, dated Sep. 16, 2024 (17 pages).

*Primary Examiner* — Chih-Cheng Kao

(74) *Attorney, Agent, or Firm* — Merchant & Gould P.C.

(57) ABSTRACT

In some embodiments, an apparatus for generating a radiation, such as X-rays, includes an emitter, such as an electron gun, of a beam of charged particles; a target, such as an anode, extending a length along a target trajectory that includes at least a curved segment and including a material adapted to emit a radiation, such as X-rays, upon the charged particles impinging on the target; and a scan tube attached to the emitter and enclosing the target. The target has multiple portions, some of which being disposed closer to the emitter than other portions. The apparatus may further include two control components. The first component includes one or more magnets for guiding the charged particle along the target without impinging on it; the second component includes one or more magnets for deflecting the guided charged particles to impinge upon the target at different locations over time.

18 Claims, 8 Drawing Sheets

(56) References Cited

U.S. PATENT DOCUMENTS

| | | | | |
|---|---|---|---|---|
| 5,490,193 | A * | 2/1996 | Kuroda | H05G 1/70 378/10 |
| 5,504,791 | A | 4/1996 | Hell et al. | |
| 5,528,658 | A * | 6/1996 | Hell | H01J 35/30 378/121 |
| 5,548,630 | A | 8/1996 | Hell et al. | |
| 5,995,586 | A | 11/1999 | Jahnke | |
| 7,340,029 | B2 | 3/2008 | Popescu et al. | |
| 7,639,785 | B2 | 12/2009 | Kirschner et al. | |
| 8,155,272 | B2 | 4/2012 | Eilbert et al. | |
| 8,530,849 | B2 | 9/2013 | Boyd et al. | |
| 10,522,262 | B2 | 12/2019 | Song et al. | |

* cited by examiner

FIG. 7
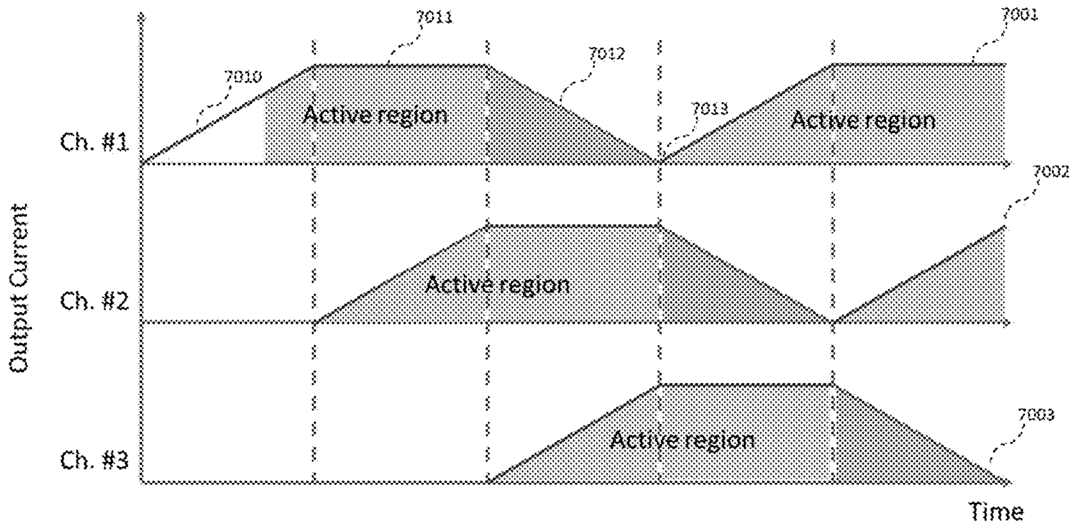
Fig. 7A
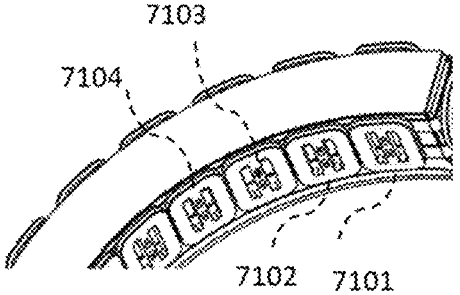
Fig. 7B

COMPACT X-RAY ELECTRON BEAM SCAN TUBE, SYSTEM AND METHOD

BACKGROUND

The present disclosure pertains to the field of high-energy electron beams, specifically to scanning electron-beam X-ray sources enabling fast scans for imaging and/or treatment devices, including computed tomography (CT) imaging systems.

X-ray imaging and treatment are extensively utilized in medical and other fields. X-ray generation in an X-ray tube is well known in the art, which includes an electron source and an anode, both enclosed in a vacuum-sealed envelope. The electron source, or electron gun, comprises a cathode to emit electrons. The anode is kept at a large positive potential relative to the cathode. The electrons are accelerated from the electron source toward the anode, forming a high-energy beam directed towards a high-atomic-number anode, such as tungsten. As electrons impinge on the anode, they decelerate rapidly, converting their kinetic energy to X-rays via the Bremsstrahlung process. The impingement point is referred to as focal spot. The resulting X-rays are transmitted out of the tube through an X-ray exit window for use in various medical and other applications.

Computed tomography (CT) is an important imaging modality. CT imaging requires the measurement of X-ray projections from multiple angles through an object, achieved either by physically moving the X-ray tube, together with a detector on a rotating gantry(the 3$^{rd}$ generation CT) or with stationary detector (the 4th generation CT), or by scanning the electron beam along an anode ring, as in Electron Beam (EB) CT with a stationary detector (the 5th generation CT as disclosed in U.S. Pat. No. 4,352,021A, its derivatives and its variations).

Many CT systems today are the 3rd generation CT, where the X-ray tube together with the detector array are mounted on the CT gantry, physically rotating around the object. However, the speed of rotation in the 3rd generation CT is limited by the centripetal forces due to the physical rotation of heavy X-ray tube with a larger moment of inertia. This limitation in rotation speed may lead to degradation (in terms of blur and errors) of the CT image caused by patient motion, such as cardiac, respiratory, and/or other organ movements. While some motion-induced blur and errors may be mitigated by reducing patient motion, such as decreasing the patient's heart rate, this often requires additional medical preparation and may include medication (such as P-blockers), resulting in significant overhead in terms of time and resources. Moreover, patients may experience side effects from the medication.

The 5th generation CT systems, as disclosed by U.S. Pat. No. 4,352,021A, its derivatives and its variations could eliminate the need to physically rotate an X-ray tube around the object. The 5th generation CT typically uses Electron Beam (EB) scan technology, namely circular anode(s) and a single electron gun with a magnetic deflection system that deflects the electron beam onto one or multiple anodes ring around the patient. Consequently, X-ray can be generated around the object by magnetically scan at a much faster rate than a mechanically rotated X-ray tube. Therefore, EB CT is less susceptible to motion-induced degradation. EB CT presents significant market potential as it eliminates the need for administering costly and potentially adverse medication. However, prior art EB CT suffers certain deficiencies. For example, U.S. Pat. No. 4,352,021A contains a large and heavy cone-shaped scan tube enclosure, which is complex to manufacture, operate, and maintain. Further, the cone-shape scan tube enclosure closes one end of the CT bore opening, greatly limiting the patient comfort, maneuverability, and accessibility, especially, limiting axial and helical (also referred to as spiral) scan. The helical scan is a standard scanning method in modern CT imaging where the patient lies on a movable table that passes through the bore opening while imaging.

U.S. Pat. No. 7,639,785B2 discloses an alternative EB scan tube design featuring a linear drift tube substantially parallel to the direction of the electron beam emitted by the electron gun and a linear anode mounted along the sidewall of the drift tube. The electrons move in a straight line until they encounter a magnetic deflection field that changes their direction. By changing the locations of the applied deflection magnetic fields at various locations along the drift tube, X-rays are generated at various focal spot positions along the linear anode. This scan tube design results in a much more compact scan tube enclosure. However, U.S. Pat. No. 7,639,785B2 suffers from the deficiency that it limits to a linear anode and is not adequately suited for CT application because the X-ray projections from a linear anode does not provide sufficient directions for adequate CT reconstruction.

There have been efforts to address the deficiencies in both prior arts by using multiple X-ray tubes with multiple electron guns, which add to complexity, inefficiency and impracticality of such CT system. These prior arts are impracticable because the electron gun is typically the least reliable part in the EB CT, thus using multiple electron guns leads to lower overall system reliability.

The current disclosure discloses a new EB scan tube design and examples of its applications, including CT application, to address the deficiencies of existing devices.

SUMMARY

The present disclosure discloses a novel charged particle scan device, including a new electron beam (EB) scan tube design suitable for CT imaging using a single electron gun and featuring a compact, lightweight, reliable, and cost-effective construction. The examples include a compact curvilinear X-ray electron beam scan tube for rapid computed tomography (CT) and other applications.

BRIEF DESCRIPTION OF THE DRAWINGS

FIG. 7A shows an example of three electric current waveforms generated by three channel current supply.

FIG. 7B shows a portion of the aiming magnets in a section of the X-ray tube; the aiming magnets are successively energized by the three electric current waveforms in FIG. 7A in some embodiments.

All drawings are for clarity; not all components or spatial relationships are illustrated to scale.

DETAILED DESCRIPTION

In some embodiments, an Electron Beam (EB) X-ray tube includes two primary components: 1) an electron gun generating and emitting electrons from a cathode in the gun, and 2) a scan tube projecting electrons onto a sequence of impingement points on an anode to generate X-rays from various directions. This trajectory of points of impingement is referred to as the anode trajectory (or the target trajectory, or the focal spots trajectory). The scan tube enclosure generally comprises three sections: 1) the entry end through which electrons from the electron gun enter, 2) the sidewall section along the centerline or length of the scan tube; 3) the opposite (or exit) end. The centerline of the scan tube is defined as the trajectory of the center points of the scan tube's cross-sections moving from one end to the other end.

Figure 1:
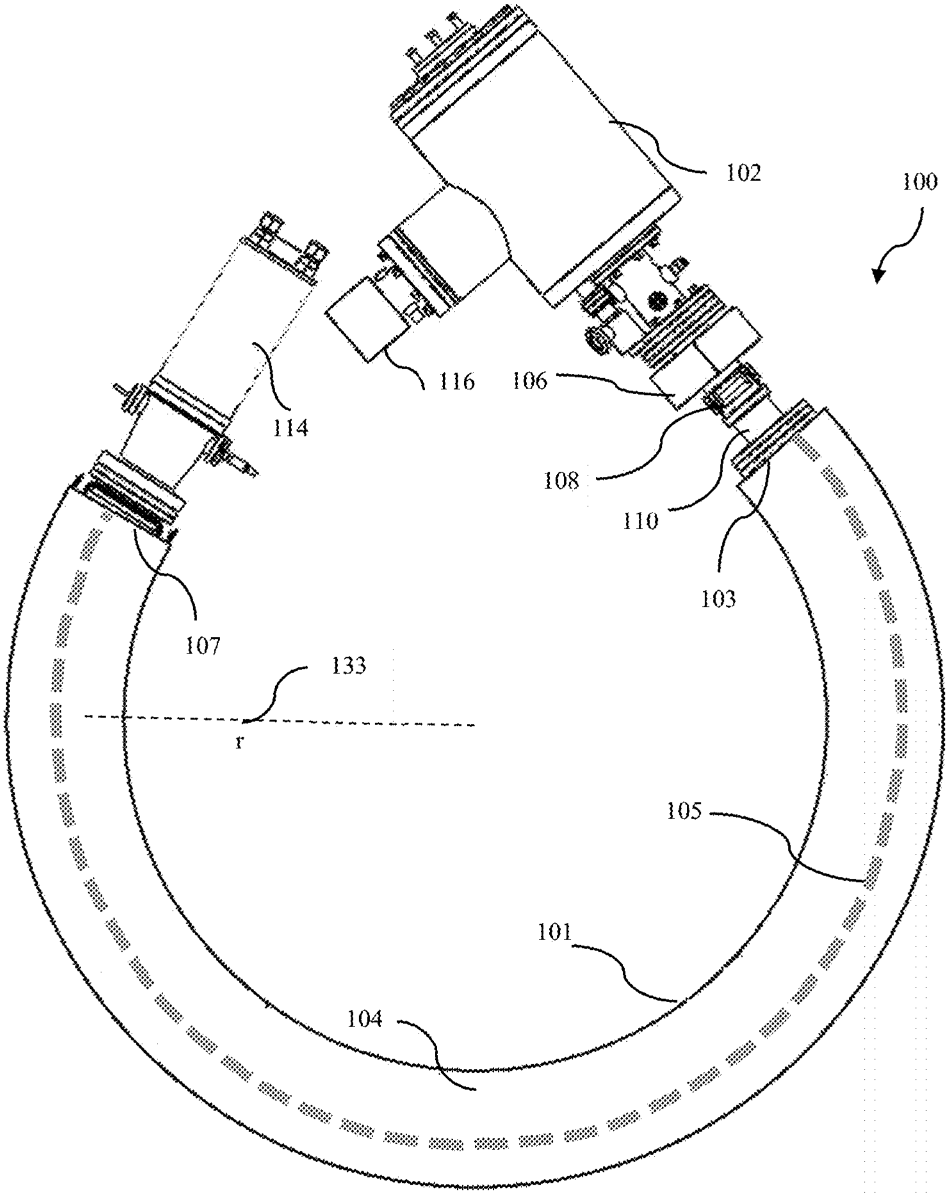
FIG. 1 is a simplified top view of an X-ray tube in certain embodiments.
Figure 2:
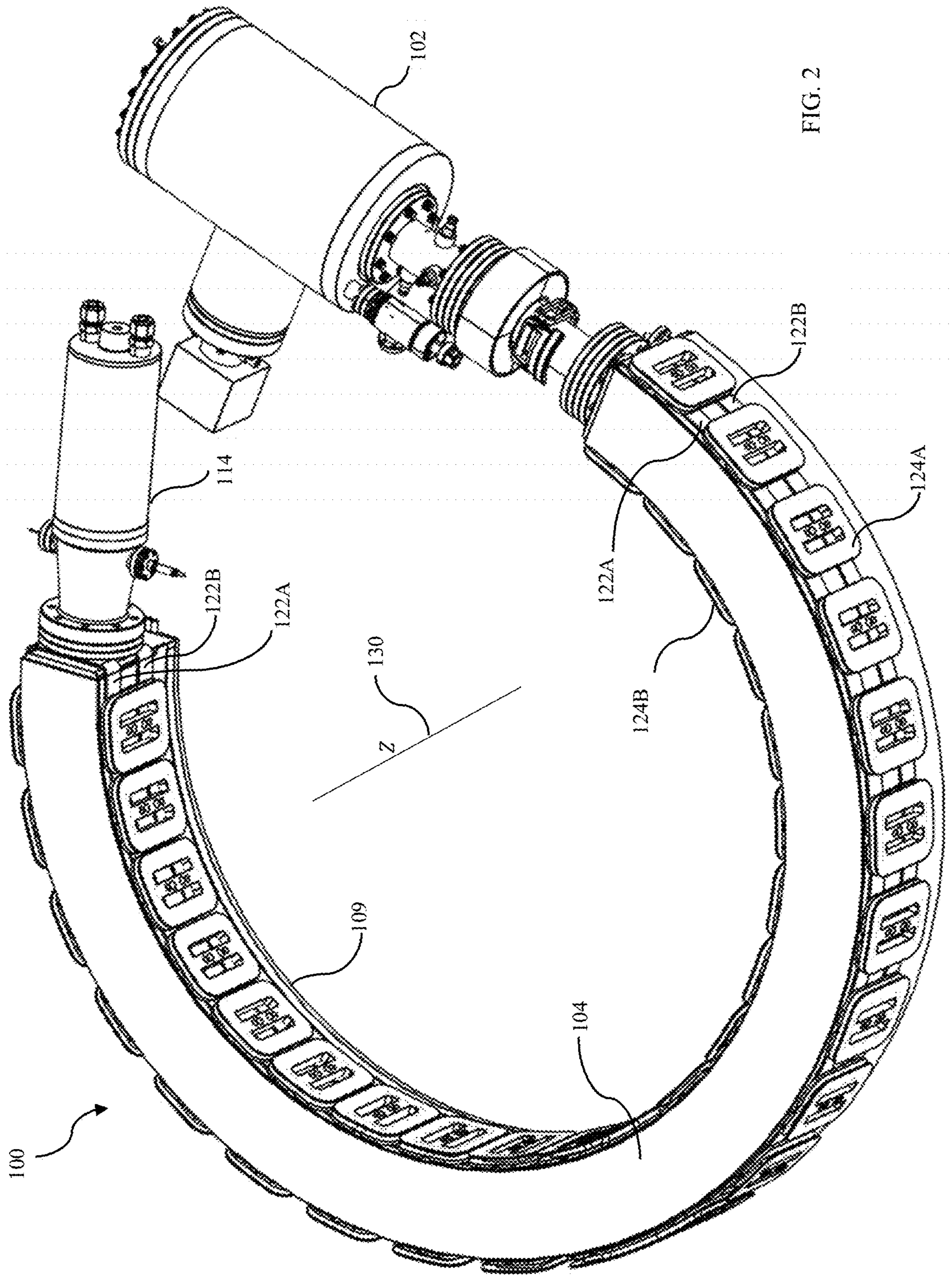
FIG. 2 is a perspective view of the X-ray tube, depicting the elements of scanning and aiming magnets in accordance with certain embodiments.

FIG. 1 provides a schematic top view of an example X-ray apparatus in certain embodiments. An X-ray Tube, labeled as 100, comprises an Electron Gun, labeled as 102 and a Scan Tube, labeled as 104. The three sections of the Scan Tube's enclosure are labeled as 103, 101, and 107, representing the entry end, the sidewall section, and the exit end, respectively. FIG. 2 is a perspective and expanded view of FIG. 1 for certain embodiments.

FIGS. 1-2 demonstrate an embodiment of a (partial) ring anode trajectory, accommodating a set of focal spots arranged in a ring trajectory, represented as a dashed shaded-band and labeled as 105 in FIG. 1.

Figure 3:
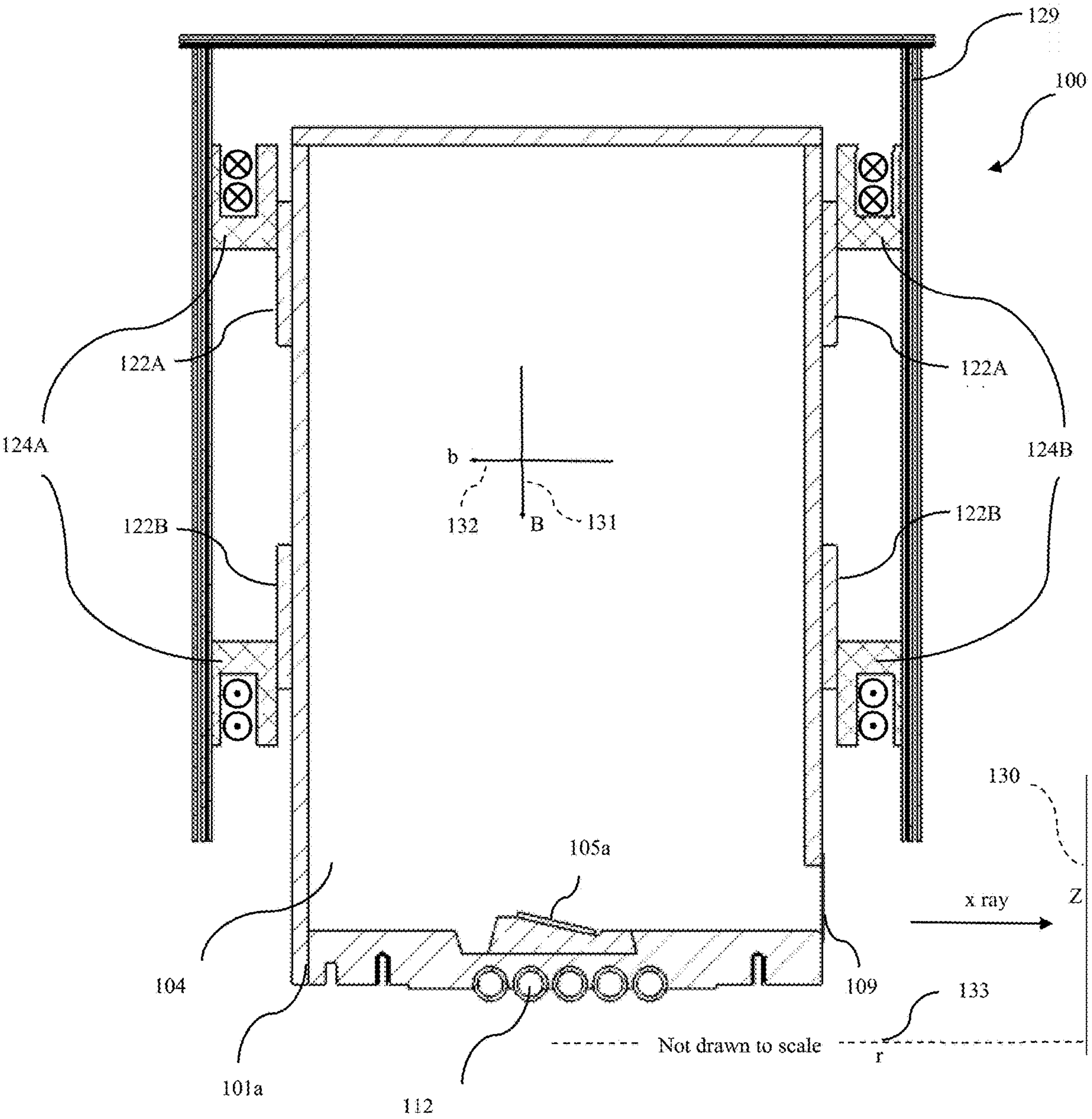
FIG. 3 is a cross-sectional and exploded view of the X-ray tube in accordance with certain embodiments, illustrating some internal elements.

FIG. 3 displays the cross-sectional view of FIG. 2, perpendicular to the anode trajectory 105. This cross-sectional view bisects the anode, revealing the anode width dimension, labeled as 105*a*, which is perpendicular to the anode's longitudinal (or ring) dimension (or the anode trajectory). The anode width dimension is also revealed by the width of the shaped band 105 in FIG. 1.

FIG. 3 also presents a cross-sectional view of the sidewall section (labeled as 101*a*) of the scan tube. (While a rectangular cross-section is shown in FIGS. 2 and 3 for one embodiment, other embodiments may include other cross-sections, such as circular or oval, for the scan tube.)

The axis of curvature of the anode trajectory (i.e., the anode ring) is illustrated as Z and labeled as 130 in FIGS. 2 and 3. The radial distance to the Z axis is illustrated as r and labeled as 133 in FIG. 1 and (not drawn to scale) in FIG. 3.

FIG. 1-3 demonstrate an example in certain embodiments. In this example, the anode ring 105 is situated and arranged along the sidewall section (or the centerline direction) of the scan tube. This is in contrast to U.S. Pat. No. 4,352,021A and its derivatives, where, the anode ring is situated and arranged on the exit end (or the base) of the conical-shaped scan tube, as opposed to along the sidewall section (or the centerline direction) of the scan tube. In other words, the configuration facilitates a good alignment (substantially parallel) between the anode trajectory (e.g., the anode ring) and the centerline of the scan tube, whereas U.S. Pat. No. 4,352,021A and its derivatives lack such an alignment, in fact, they are almost perpendicular to each other. Given that the anode ring typically has a large radius (half a meter or more), while the centerline (or the length) of the scan tube is typically a few meters long, a better alignment between these two trajectories (anode ring and the centerline of the scan tube) has a significant impact on the shape and size of the scan tube. As a result of the disclosed embodiments, the scan tube enclosure is a compact, toroidal-shape enclosure due to the designed alignment of two trajectories. In contrast, the scan tube disclosed in U.S. Pat. No. 4,352,021A and its derivatives is a bulky, conical-shaped scan tube enclosure due to lack of (in fact, almost 90 degrees off) the alignment of the two trajectories.

In certain embodiments, the configuration further ensures a compact placement of the scan tube and the electron gun into a toroidal shape enclosure similar to a conventional CT gantry so that the central opening of the toroidal shape enclosure (commonly referred to as the imaging bore of the CT) can be fully open and accessible at both ends, as shown in FIGS. 1 and 2. Such a feature is difficult, if not unachievable, to attain by a configuration of the kind disclosed in U.S. Pat. No. 4,352,021A and its derivatives, as its conical-shaped scan tube imposes one closed end of its CT imaging bore. Bore opening at both ends has the advantage of providing increased patient comfort, accessibility, and maneuverability. It facilitates a large range of axial and helical scan and patient positioning during the imaging procedure, accommodates larger patients or medical equipment, such as when imaging is required during surgical procedures or interventional radiology, and minimizes feelings of claustrophobia.

In certain embodiments, the configuration further ensures a placement of the electron gun close to the anode, with the closest distance to the anode trajectory being less than 20 cm in some examples, as shown in FIGS. 1 and 2. In contrast, the system disclosed in U.S. Pat. No. 4,352,021A and its derivatives cannot achieve this proximity, with its closet distance between the electron gun and anode around 200 cm.

In some embodiments, the configuration further ensures the direction of the electron gun (i.e., the direction of entry electrons) and initial anode trajectory to be aligned within an angle of typically less than, for example, 20, 10, or 5 degrees, as shown in FIGS. 1 and 2. By comparison, the system disclosed in U.S. Pat. No. 4,352,021A and its derivatives lack such alignment, resulting in the angle between the electron gun and the anode trajectory to be between 45 and 90 degrees. In some embodiments, the direction of entry electrons is substantially perpendicular to the axis of curvature 130 of the anode trajectory 105. In other embodiments, the direction of entry electrons is substantially parallel to the anode trajectory 105.

The alignment of the anode trajectory with the centerline of the scan tube and with the electron gun enables X-ray tube in certain embodiments more compact, which can fit into a toroidal-shaped enclosure, resulting in a fully open central opening of the toroidal shape enclosure (or the imaging bore in CT application) that is accessible at both ends. Such open access is difficult, if not impossible, to attain in systems similar to that disclosed in U.S. Pat. No. 4,352,021A and its derivatives.

Figure 4:
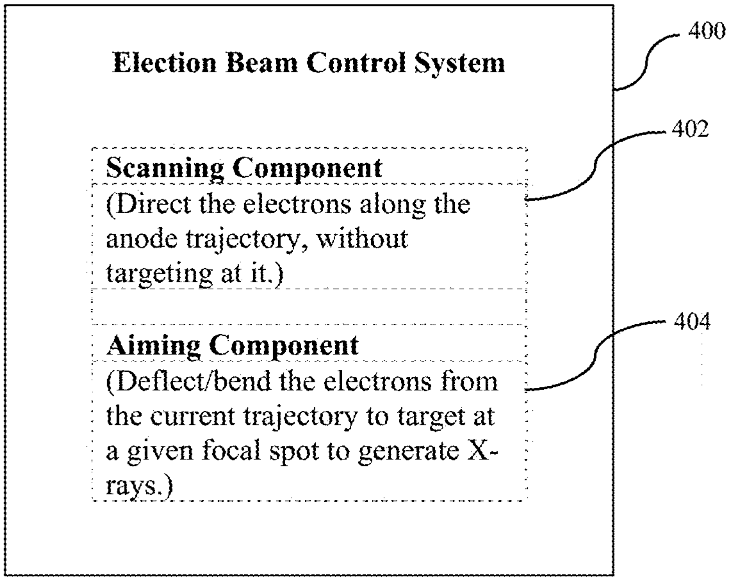
FIG. 4 illustrates two components of the electron beam control system in certain embodiments. They are Scanning Component and Aiming Component

In some embodiments, an additional control, or guiding, component, referred to in this disclosure as the scanning control component, is used in generating X-rays disclosed herein. In some embodiments, separate control components, namely, the scanning and aiming components are used. In an example shown in FIG. 4, a controller 400 includes a scanning component 402 and an aiming component 404. The function of the scanning component 402 is to direct the electrons along a path around the curved anode trajectory without impinging on the anode or on the sidewalls of the scan tube. The function of the aiming component 404 is to deflect/bend the electrons from the current trajectory to targets at given focal spots on the anode to generate X-rays.

In one embodiment, the scanning control component employs one or more magnets, referred to as the scanning magnet, to guide the electrons within certain distance of the anode trajectory 105 without impinging on it. Under this embodiment, in one embodiment, such a distance is within 50 cm. In one embodiment, the trajectory of electrons is substantially perpendicular to the axis of curvature 130 of the anode trajectory 105. In another embodiment, the trajectory of electrons is substantially parallel to the anode trajectory 105. The scanning magnets may be placed outside, proximal to, Scan Tube 104.

In one embodiment the scanning magnet is exemplified by a Helmholtz coil illustrated by two windings, Winding 122A and Winding 122B in FIGS. 2 and 3. When the scanning magnet is energized, current flows through the windings, generating a scanning magnetic field, illustrated as $\vec{B}$ and labeled as 131 in FIG. 3, within specific interior regions inside Scan Tube 104 where the electron beam is expected. In this example, the scanning magnetic field $\vec{B}$, which along the axis of curvature, causes the electrons to rotate in a circular orbit with a radius of r, according to the well-known physics equation $$r = \frac{mv}{qB}.$$

Thus, the scanning control component guides the electrons to travel in an orbit in the vicinity of the anode trajectory 105 without impinging on it.

In one embodiment, the aiming control component utilizes a series of magnets, referred to as the aiming magnets, to direct the electrons to target at a specific focal spot on the anode trajectory 105, generating X-rays. The aiming magnets may be implemented using a series of Helmholtz coils with windings wrapped around a set of non-magnetic yokes. As an example, two such yokes, Winding Form 124A and Winding Form 124B, are illustrated and labeled in FIGS. 2 and 3. The aiming magnets may be placed outside, proximal to, Scan Tube 104. The aiming magnet applies the aiming magnetic field, depicted as b and labeled as 132 in FIG. 3, to deflect or bend the electron beam from its current trajectory to target at a specific focal spot on the anode trajectory 105, producing X-rays. When multiple aiming magnets are energized, the aiming magnetic field $\vec{b}$ becomes the superposition of the fields generated by each magnet.

The separation of two control components of electron beam control system, namely, scanning and aiming, where aiming is distributed along the anode trajectory and occurred at a close distance to the impinging point, stands in contrast to U.S. Pat. No. 4,352,021A and its derivatives where aiming occurs at roughly single point near the entry end of the scan tube (the apex of the cone), which is far (around 200 cm) from the focal spot to be targeted (on the base of the cone). Distributing the aiming points along the anode trajectory brings them closer to the impinging point thus shortening the portion of the trajectory outside of the magnetic fields. This results in a more compact design and a tighter electron beam.

One important application of EB X-ray tube is its CT application. CT application requirements include 1) to use an adequate anode trajectory, preferably a ring trajectory to achieve the required angular coverage of 180 degrees plus the fan beam angle around the Region of Interest (ROI), to collect X-ray projections from sufficient angles for adequate CT reconstruction; 2) to use a simple X-ray source with, preferably, a single electron gun, because using multiple electron guns add to complexity, inefficiency and impracticality of such CT system.

The prior art disclosed in U.S. Pat. No. 4,352,021A and its derivatives meets the above CT application requirements. In contrast, an alternative EB scan tube design disclosed in U.S. Pat. No. 7,639,785B2 does not meet the requirements because it is designed only for a linear anode, whereas X-ray projections from a straight line is insufficient for adequate CT reconstruction. Furthermore, other prior arts proposing to reduce the deficiencies of U.S. Pat. No. 4,352,021 or U.S. Pat. No. 7,639,785B2 by using multiple X-ray sources with multiple election guns fail to meet the above requirements. These prior art systems are impracticable because the electron gun is typically the least reliable part in the EB CT, thus using multiple electron guns leads to lower overall system reliability. Thus, the various embodiments can be more directly compared with U.S. Pat. No. 4,352,021A.

The devices and systems in certain embodiments address the deficiencies in prior arts by using a single electron gun with a curvilinear anode trajectory (e.g. an anode ring trajectory). Thus, the devices and systems meet the above CT application requirements more fully. Furthermore, the embodiments include the scanning component of the electron beam control system, which is lacking in prior arts, to track the curvature of the anode trajectory.

Figure 5:
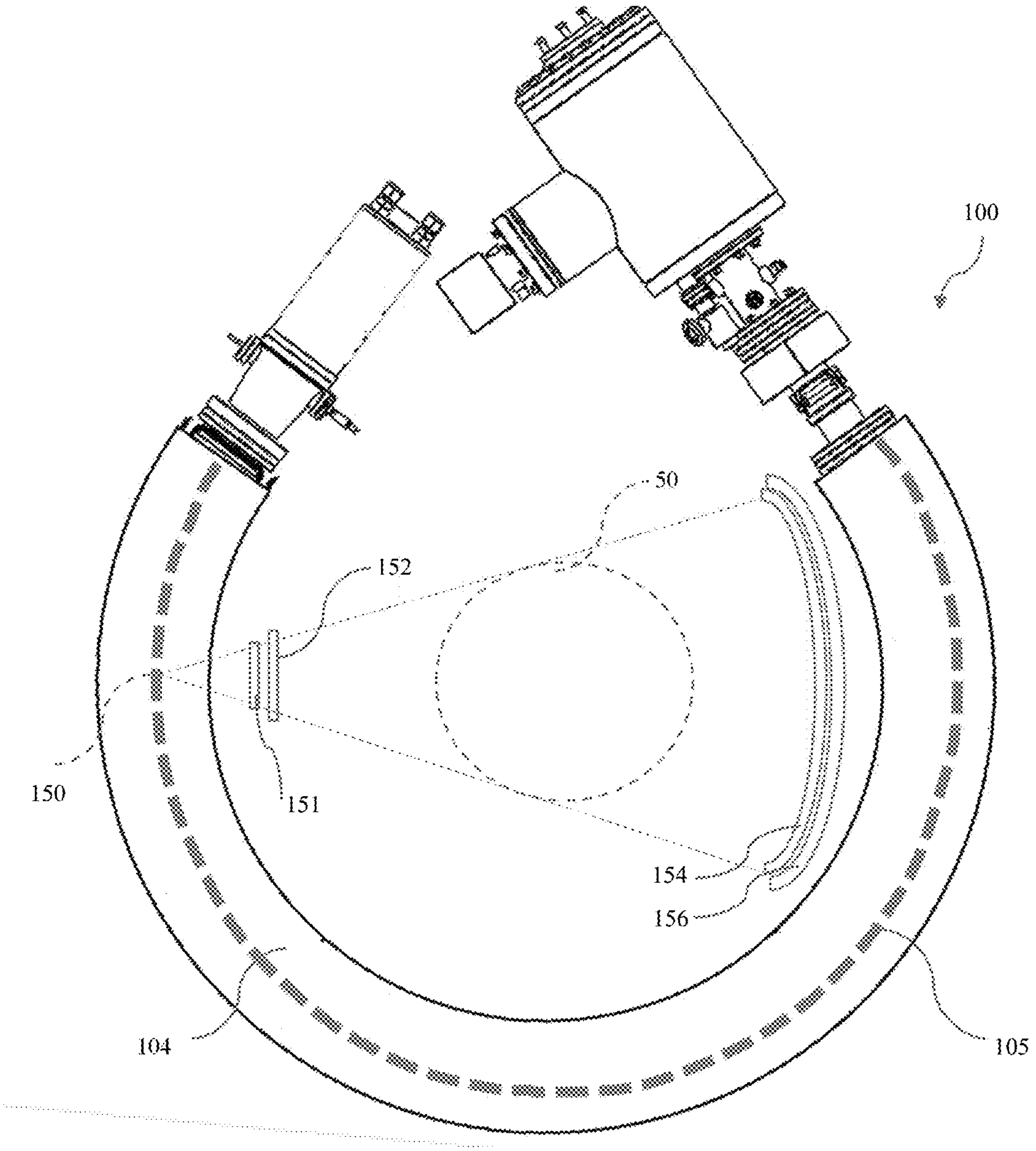
FIG. 5 shows one embodiment of CT application of the X-ray tube.

In certain additional embodiments in CT application, as shown in FIG. 5, other components may be used to measure X-ray projections from various rotational angles around the Region of Interest (ROI), illustrated and labeled as 50. These other components may include the following: 1) the X-ray filter, illustrated and labeled as 151, to moderate the intensity distribution and/or the energy spectrum of the X-ray generated. For example, a bowtie filter may be used to reduce the dose to the patient by attenuating those X-rays that pass through less attenuating regions of the body; 2) the X-ray pre-object collimator, illustrated and labeled as 152, to limit the extent or the dimensions of X-rays beam exited from the X-ray windows 109; 3) the X-ray detector, illustrated and labeled as 156, to measuring the X-rays received. The X-ray detectors include energy-integrating detectors (EIDs) and photon-counting detectors (PCDs) for some embodiments. 4) X-ray post-object collimator, illustrated and labeled as 154, which preferably accepts those X-rays passing straight through the object to be detected by 156 and preferably rejects all other X-rays, such as scatter. Furthermore, two sets of the other components, with a rotational angle offset between the two sets and each set as illustrated FIG. 5, may be used.

In medical CT scanners, these other key components are mounted on a gantry (commonly referred to as CT gantry) together with an X-ray tube to rotate around the Region of Interest 50. This case is referred to as the 3rd generation CT.

In one embodiment, the rotation of an X-ray tube around ROI 50 can be achieved by EB scanning along the anode ring 105 inside X-ray Tube 100, thus physical rotation of a X-ray tube 100 around ROI 50 is no longer necessary. This embodiment is referred to as the stationary X-ray tube. In this embodiment, the other key components, such as X-ray detector, can be mounted stationary (without rotation).

In some embodiments, while X-ray Tube 100 is stationary, at least one set of other components, for example, X-ray detector 156, X-ray filter 151, or X-ray collimator 152 or 154, or any combination is mounted on a rotational gantry. The rotating components rotate in synchronization with, i.e., being fixed relative to, the sequential movement of the focal spot (one shown as 150) along the target ring 105.

In some embodiments, coordination, or synchronization, of the movement of focal spots 150 in the stationary tube 100 with the rotating gantry is achieved by dynamically adjusting and timing the field in the aiming magnets based on the rotational position signal of the gantry received optically or other way. In other embodiments, the rotational speed of the gantry can be continuously adjusted based on the electron beam sensor information.

In some other embodiments, the X-ray filter 151 is equipped with an adjustable aperture. The aperture is dynamically adjusted to modulate the X-ray dose delivered at each angle based on predetermined delivery scheme that minimized dose while maintaining suitable level of image noise. The aperture in some embodiments is adjusted by means of a rotating disk with a slit cut into it, where the width of the slit varies along the perimeter of disk. Rotating the disk changes the width of the opening in the disk thus varying the amount of X-ray radiation going into the patient. In some embodiments, the rotating disk with a slit is paired with a stationary disk with another aperture for improved collimation efficiency.

In some embodiments the detector 156 is also rotated with the gantry. This allows to reduce the length of the detector arc, thus reducing the count of detector pixels. In one embodiment the detector is powered using slip ring mechanism, which is also used to read out the detector data to the reconstruction computer. In another embodiment, the detector is powered autonomously through an energy storage device, such as a battery. In this embodiment, the detector signals can be read out from the detector using wireless communication technology.

The combination of stationary (for at least X-ray Tube 100) and rotational components described above has multiple advantages over both the 3rd and 5th CT generations. The CT apparatus disclosed in the present disclosure can achieve faster scan speeds compared to the 3rd generation CT (roughly, 50 ms or faster vs 200 ms) due to a much smaller moment of inertia to be rotated, because the X-ray source, which accounts for a majority of the inertia in the 3rd generation CT, is stationary. At the same time, the CT apparatus disclosed in the present disclosure inherits the advantages of the 3rd generation CT in dose efficiency, dynamic range and reduced detector count.

Certain embodiments disclosed herein pertains to general EB scan technology that may be used in a multiview imaging, a tomosynthesis imaging, a CT imaging, or any combined imaging. For the embodiment of CT imaging with a rotating detector, it differs from $3^{rd}$ generation CT because of using a stationary x-ray tube. It also differs from $5^{th}$ generation CT because of using a rotating detector. Even for the embodiment of CT imaging with a stationary detector, it still differs from the $5^{th}$ generation CT as disclosed in U.S. Pat. No. 4,352,021A and its variations and derivatives because the new EB scan technology disclosed herein has a designed alignment between the anode trajectory and the direction of the electron beam until deflected toward the anode, with an angle of the two directions being less than, say, 20 degrees. In contrast, the EB technology in $5^{th}$ generation CT (namely U.S. Pat. No. 4,352,021A and its variations and derivatives) lacks such a designed alignment, thus the alignment is almost 90 degrees off.

While the scan tubes disclosed in the examples above have a ring anode, scan tubes with anodes of other shapes can be used. For example, curvilinear anodes, i.e., an anode inside the sidewall section of the scan tube and extending over the length (or centerline) of the section of the scan tube to form (or arrange) the anode trajectory, containing at least a curved anode trajectory. A curvilinear anode trajectory may include 1) a ring (segment) as discussed previously, 2) multiple curves; 3) a curve with either or both ends attached to a line; 4) two curves connected by a line, 5) and others.

In some embodiments, the X-rays generated by X-ray Tube 100 exit the tube through an X-ray Window, illustrated and labeled as 109 in FIG. 2 (for those not blocked) and FIG. 3. X-ray Window 109 in this example, is a slit opening towards the ROI around the Z axis. "Slit opening" in this context means a substantially transparent to X-rays; the physical structure of the slit opening includes, in some embodiments, an X-ray window made of any suitable material, including materials used for X-ray windows in conventional X-ray tubes. A cross-sectional view in FIG. 3 only shows the z opening of X-ray Window 109, which determines the z coverage of the object.

Figure 6:
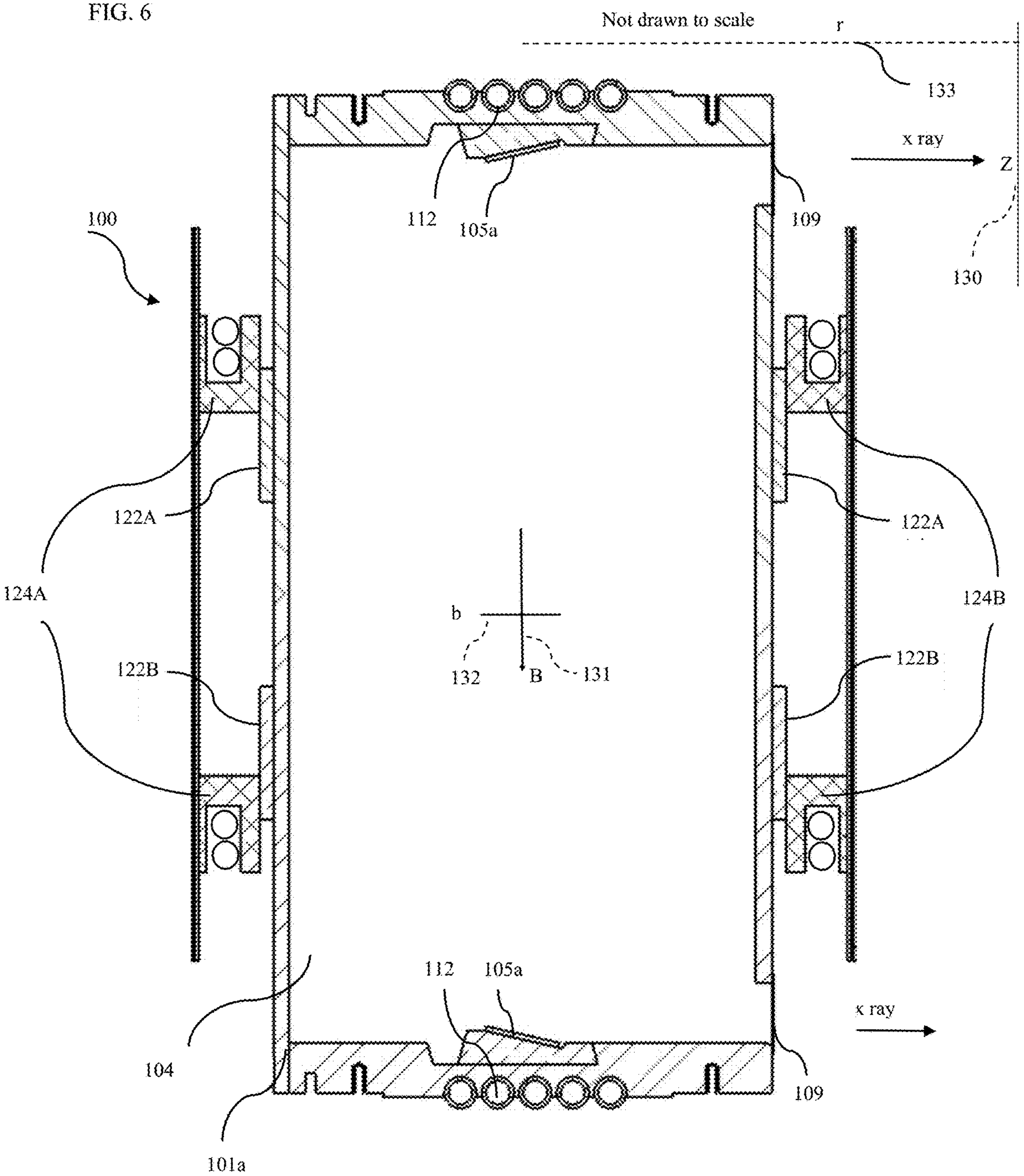
FIG. 6 presents an alternative embodiment of FIG. 3 with the anode mounted on both the top and bottom of the scan tube.

FIGS. 2 and 3 show an embodiment that the anode 105 and therefore X-ray Window 109 are arranged near the bottom (relative to the axis of curvature Z) of the scan tube sidewall section. An alternative embodiment is that the anode 105 and X-ray Window 109 are arranged near both the top and the bottom of the scan tube sidewall section, which can be similarly implemented, as illustrated in FIG. 6. In this embodiment, the direction of the scanning magnetic field, B, will stay the same, aligned with the axis of curvature Z. However, the direction of the aiming magnetic field, b flips to target the elections at either anode (near top or bottom). This embodiment may be used to extend the object z coverage using multiple anodes at various z locations without increasing the z extent of the detector array.

Furthermore, multiple anodes may be used on the same sidewall section (say at the bottom) of the X-ray Tube 100, but at different radial distance r to the Z axis. Specifically, by selecting different strengths of the scanning magnetic field $\vec{B}$ 131, the electrons rotate in different circular orbit with different radial distance r according to the above equation. Once the aiming magnetic field $\vec{b}$ 132 is applied, the electrons will impinge upon the anode at different radial distance r to the Z axis. Anodes at different radial distance may be offset in z (for example, by amounting on different stand-off structures), thus generating X-ray at different z locations for the benefit described above.

In one embodiment, modulating the scanning magnetic field $\vec{B}$ 131, and/or the aiming magnetic field $\vec{b}$ 132, to control the focal spots positions can also be used to achieve increased sampling rate along the anode and/or in z direction, resulting in the increased image spatial resolution.

In some embodiments, aiming magnetic field is contained within field region of Scan Tube 104 by placing permalloy or other magnetic material with ultra-low hysteresis characteristics around magnets so that the magnets share the continuous magnetic return. A common form of the material used for such applications is called mu-metal. In the embodiments of FIG. 3, mu-metal, labeled as 129, is adjacent to the aiming magnet and may be attached directly to the winding forms of the aiming magnet.

For simplicity of illustration, FIG. 3 illustrates only two turns of wire for each winding of the aiming magnet comprising Windings 124A and 124B. Embodiments may have aiming magnets with more or less turns of wire. Standard symbols are used to indicate the direction of positive current flow in these windings, where ⊗ or ⊙ indicates a direction pointing into or out of the page of the drawing respectively. With the directions of positive current flow in Windings 124A and 124B as indicated in FIG. 3, the aiming magnetic field $\vec{b}$ will, at certain interior region of Scan Tube 104, point in a direction parallel with the radial direction $\vec{r}$ so that an electron is targeted to the trajectory of the focal spots 105.

The embodiments described above may contain magnetic Lens, 106, and a quadrupole magnetic lens, Quadrupole Lens 108, positioned about a Coupling Tube 110 illustrated in FIG. 1.

In some embodiments, Lens 106 and quadrupole 108 comprises dynamically and separately adjusted (driven) coils resulting dynamically focused and shaped electron beam emitted by Electron Gun 102. As the location of the electron beam impact on the anode changes, the electron travel distance changes and therefore the focal distance changes. Dynamical adjustment of the Lens 106 and quadrupole 108 accounts for these changes.

In some embodiments, the magnets are electromagnets, i.e., windings or sets of windings forming electromagnets with or without magnetic returns. For example, a magnet may be an electromagnet comprising turns of wire about Scan Tube 104. In some embodiments, the magnet comprises a Helmholtz coil, including two sets of windings separated by a sufficient distance. In other embodiments, permanent magnets, or a combination of permanent magnet(s) and electromagnets, are used. For example, one or more permanent magnets or electromagnets may be positioned adjacent to the scan tube and moved along the scan tube to move the focal spot along the anode trajectory. In some embodiments, one or more permanent magnets or electromagnets and an X-ray detector can be mounted at opposing ends of the rotating bracket.

The aiming magnets are energized in such order as to target electrons toward various positions along the anode trajectory 105. Each aiming magnet may be independently energized or driven, so that any number of aiming magnets may at any time be independently energized to generate a magnetic field.

For clarity of illustration, FIG. 2-3 does not show connections between windings in a deflection (aiming) magnet. For example, in some embodiments, the winding pairs (such as Winding 124-1A and 124-1B) may be electrically connected to form a Helmholtz coil, so that one driver may be utilized to energize both windings. In some embodiments, they may not be electrically connected to each other and may be driven independently by multiple drivers, or by a driver with two or more independent output stages.

Energizing one or more aiming magnets deflects an electron beam to the anode trajectory 105. The positions on the anode trajectory 105 to which electrons are targeted (i.e., the focal spots) depend upon the superposition of magnetic fields from these magnets. One or more drivers coupled to the aiming magnets may be used to provide dynamically adjusted values of current to the aiming magnets to target an electron beam to various positions on the anode trajectory 105.

Some embodiments energize the aiming magnets in sequential fashion so that groups of aiming magnets are energized at a time to target an electron beam impact point along the anode trajectory 105 so that a focal spot is essentially swept/scanned along the anode trajectory 105. In this way, an embodiment may find application in a tomosynthesis or CT X-ray scanner, where X-rays are generated along a curve surrounding a patient. Furthermore, the aiming magnets may be broken into more than one subgroup energized in sequential fashion within each subgroup so that the movement of focal spot due to each subgroup is essentially swept/scanned along the anode trajectory.

Because only one or a few subsets of aiming magnets are energized at any moment during the operation, the controller in some embodiments include a multiplexing circuit that connects the output of the power supply to the particular subsets of magnets to be energized at the moment.

For example, FIG. 7 shows the time sequence of three electrical currents produced by a single three-channel current driver. Current waveforms 7001 energizes coil 7101; current waveform 7002 energizes coil 7102; and 7003 energizes coil 7103. The field sensed by the electron beam is an integral of superposition of the fields created by coils 7101, 7102 and 7103. During ramp time 7010, only coil 7101 has current flowing through it producing the field to deflect the beam. When current 7001 reaches the plateau, current 7002 is ramped during time 7011, while current 7001 stays constant. During this period both coils 7101 and 7102 produce the magnetic field to deflect the electron beam and aim it at the focal point on the anode. When current 7002 reaches the plateau, the current 7003 energizing coil 7103 starts to linearly increase. At this point the electron beam does not reach the region of coil 7101 and thus the field in that coil is irrelevant to the aiming of the beam. Therefore, the current 7001 in coil 7101 can be safely reduced to zero. The electron beam is instead affected by currents 7002 and 7003 in coils 7102 and 7103.

At some point during the ramped down of current 7001, its corresponding magnet is switched from 7101 to 7104. This can be done when the current is close zero or at point 7013 to reduce the current in the switched associated with the stored energy in coil 7101.

After time point 7013 current 7001 is increased again. However, it is now coils 7102, 7103, and 7104, with currents 7002, 7003, and 7001, respectively, that affect aiming of the electron beam. The process of switching currents to successive aiming coils continues until all magnets along tube 701 are addressed and the beam covers the full anode trajectory.

In other embodiments, current waveforms 7001, 7002 and 7003 can be chosen differently to conform to such factors as desired motion profile and speed of the focal spot, shape and size of the anode and other geometrical considerations.

Some embodiments may have fewer than three current waveforms, whereas other embodiments may have more than three waveforms, for each focal spot.

Figure 8:
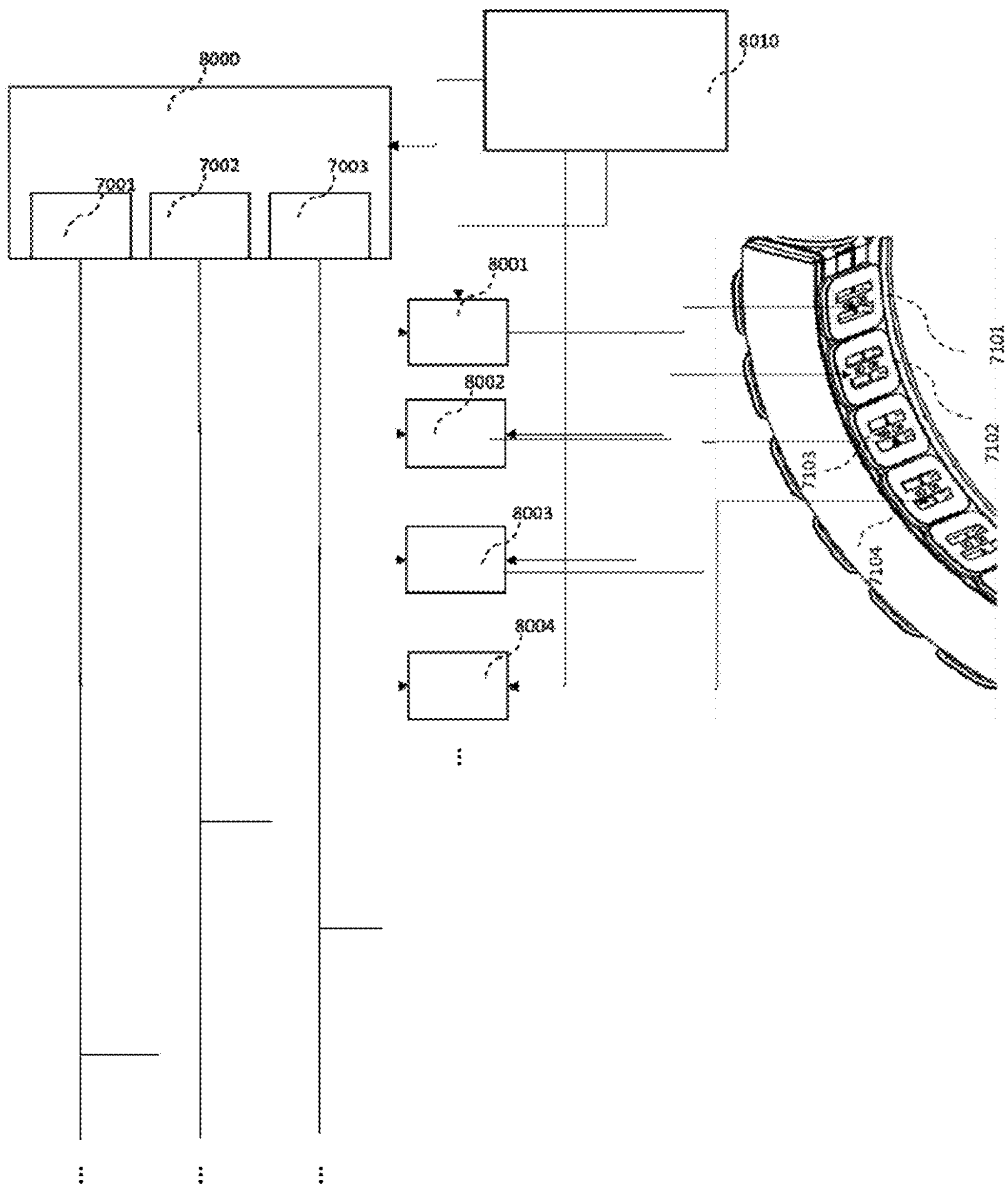
FIG. 8 shows and example of a control circuit, including a multiplexing circuit, for sequentially selectively distributing power to the aiming magnets.

The dynamic switching of the current driver output can be achieved using any suitable circuit. For example, in the example shown in FIG. 8, the current driver 8000 with three outputs produces currents waveforms 7001, 7002, 7003 based on the timing information from the control device 8010. The outputs of driver 8000 are wired into a series of switches, where each switch corresponds to an aiming magnet coil. In the embodiment shown in FIG. 8, switches 8001, 8002, 8003 and 8004 are wired to aiming magnets 7101, 7102, 7103 and 7104 respectively. The same controller that sets up the timing of the waveforms 7001, 7002 and 7003 is configured to close and open switches 8001, 8002, 8003 and 8004. When the switch is closed, the current flows through the switch. When it is open, the current flow stops. In this embodiment, if the switch 8001 is closed and switch 8004 is open output current 7001 flows to coil 7101. When switch 8001 is open and switch 8004 is closed the output current 7001 flows to coil 7104.

In some embodiments only one switch from the set connected to a single output of 8000 is closed. In other embodiments, each output may be split into multiple coils by closing multiple switches simultaneously.

Some embodiments may employ solid state switches, while others may use electro-mechanical switches. Some embodiments may use a combination of two.

Some embodiments may use a digital or analog control device 8010.

Some embodiments may use multiple control devices 8010.

It should be noted that embodiments may include anodes positioned differently than that illustrated in the several drawings, and it is only a matter of orienting the aiming magnets (or adding additional aiming magnets) so that their respective magnetic fields as experienced by the electrons have the proper magnitude and direction to target the electrons to the desired positions on the anode to generate X-rays.

In the embodiments of FIG. 2, Winding 122A and 122B are electrically connected to each other, as may be observed by noting that at the end of Scan Tube 104, turns of the two windings wrap around an edge so that Winding 122A and Winding 122B are electrically connected to each other. In another embodiment the scanning magnet Windings 122A and 122B are electrically separated and are individually driven.

Similarly, two winding pairs, such as 124A and 124B in FIGS. 2, 3, and 6, may be electrically connected to each other, so that two terminals are available for connection to a driver for energizing the aiming magnet. For clarity of illustration, FIG. 2 does not show the wire making up the windings and does not show the electrical connections.

In the drawings, the aiming magnetic field $\vec{b}$ provided by aiming magnets at various positions along anode trajectory 105, for example, are in a direction parallel to the axis of curvature or in a radial direction orthogonal to the axis of curvature. However, the orientations of the aiming magnets may vary from embodiment to embodiment, as well as within an embodiment. For example, for some embodiments there may be multiple aiming magnets with varying orientations.

For aiming magnets that are of the Helmholtz coil type, aiming magnetic field $\vec{b}$ at an interior region where the electron beam is expected may be taken to be parallel to its axis of symmetry. Accordingly, some embodiments may be described as comprising a set of aiming magnets where each aiming magnet has an axis of symmetry along a radial direction from some point (the same point for each aiming magnet) on the axis of curvature.

The term Helmholtz coil is generalized herein to include magnets having two sets of windings parallel to each other, but where the relationship of their diameters to their separation distance need not satisfy the classical definition of a Helmholtz coil. Furthermore, a set of windings need not be circular in form but may take any arbitrary planar shape.

The magnets do not need to be comprised of Helmholtz coils. Any suitable combination of winding may be used. For example, any combination of windings that provide uniform dipole magnetic field may be used to accomplish described electron beam guiding.

In a case where X-ray Tube 100 is powered but no X-ray exposure is desired, for example during the pause of a patient x-ray scan, the electrons travel through the entire length of Scan Tube 104 without impinging on the focal spots 105 and are absorbed and terminated at Collector labeled as 114 in FIG. 1. Collector 114 includes sufficient material to terminate the electron beam and contains proper shielding to prevent unwanted radiation from escaping. Collector 114 will be referenced and shown as a separate component coupled to Scan Tube 104 even though it may be integrated with Scan Tube 104. X-ray Tube 100 may be more easily repaired or serviced when Collector 114 is coupled to Scan Tube 104 rather than when integrated with it. Collector 114 and Scan Tube 104 may be electrically isolated and may include electrical connectors to measure the full collected electron beam charge.

The heat created by the anode or Collector 114 may be removed by running water or other cooling liquid through them, or air cooled if sufficient time between irradiations is provided.

An ultra-high vacuum (UHV) pump, Pump 116, is coupled to X-ray Tube 100, and is coupled directly to Electron Gun 102 in the embodiments of FIG. 1. Other embodiments may have one or more UHV pumps coupled to other components of X-ray Tube 100. During operation, Pump 116 keeps interior regions (e.g., those regions through which the electron beam travels) of Electron Gun 102, Scan Tube 104, Coupling Tube 110, and Collector 114 in the UHV regime, usually characterized by a pressure in the 0.1 to 100 micropascal (μPa) range.

An anode, also referred to as an anode, may comprise a mixture of tungsten and other materials, and in some embodiments is held at ground electrical potential. Electron emits electrons with the kinetic energy in the range from few keV up to several MeV depending on applications.

While the foregoing examples involve X-ray sources, with an electron gun and anode, other radiation sources can be similarly devised. In general, a radiation source can have a similar configuration as the X-ray tubes described above, but with an emitter of a different type of charge particles than electrons and a scan tube enclosing a target that is appropriate for generating the desired radiation upon impingement of the charged particles. Similar scanning and aiming components as described above can be used.

The phrases "or" is used in accordance with formal mathematical logic. Relating a measurable aspect of an embodiment (e.g., length, angle, time, magnetic field) to a numerical value or vector, relating by an equality or equivalence a measurable aspect of an embodiment to another measurable aspect (e.g., that a set of focal spots on an anode are in a curvilinear geometry), or describing an aspect as constant or uniform (e.g., a uniform magnetic field over some interior region of the tube) is accurate to within accepted tolerances as practiced in the relevant art; accordingly, the qualifiers "substantially" or "substantially constant" or the like for a numerical quantity, vector, or relationship are not needed when describing embodiments or reciting a claim element.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. An apparatus, comprising:

an emitter of a beam of electrons;

a target extending a length along a target trajectory that includes at least a curved segment and comprising a material adapted to emit X-rays or gamma radiation upon the electrons impinging on the target, the target having a first end portion disposed proximal to the emitter and a second end portion distal to the emitter;

a scan tube attached to the emitter and enclosing the target; and a collector disposed adjacent to the second end and adapted to receive at least a portion of the electrons from the emitter, the collector being electrically isolated from the scan tube and adapted to be connected for measuring the electric charge produced by the received electrons.

2. The apparatus of claim 1, wherein the first portion of the target extends in a first direction, and the emitter is adapted to emit the beam of electrons into the scan tube in a second direction forming an angle of no more than about 20 degrees from the first direction.

3. The apparatus of claim 1, wherein the scan tube has a toroidal shape defining a center opening, the apparatus further comprising an enclosure enclosing the scan tube, the enclosure defining a center opening within the center opening of the scan tube, wherein the center opening of the enclosure defines an axis passing through the center opening of the enclosure and is accessible from both sides along the axis.

4. The apparatus of claim 1, further comprising a plurality of magnets adapted to control direction of motion of the electrons.

5. The apparatus of claim 4, wherein a first subset of the magnets is adapted to guide the electrons in a trajectory inside the scan tube without impinging on the target or sidewall of the scan tube, and a second subset of the magnets is adapted to deflect the electrons from their guided trajectory toward the target.

6. The apparatus of claim 5, further comprising a magnetic return, wherein the magnets share the magnetic return.

7. The apparatus of claim 5, wherein at least the second subset of the magnets comprise a plurality of electromagnets disposed along the scan tube.

8. The apparatus of claim 7, further comprising a controller adapted to energize the plurality of electromagnets, each with a respective waveform, to generate a composite magnetic field for deflecting the electrons from their guided trajectory toward the target at a time-varying location.

9. The apparatus of claim 8, wherein the controller comprises a power supply and a control circuit, the power supply being adapted provide power to energize a subset, but not entirety, of the plurality of electromagnets, the control circuit being adapted to sequentially apply the power provided by the power supply to different subsets of the electromagnets.

10. The apparatus of claim 5, wherein the second subset of the magnets comprises a plurality of magnets, each configured to generate a respective magnetic field in a respective second direction substantially transverse to the direction of a magnetic field generated by the first subset of the magnets, to cause a movement of location where the electrons impinge on a respective plurality of portions of the target.

11. The apparatus of claim 1, further including a cooling system for the target.

12. A scanning electron beam X-ray scanner, comprising:

a scanning electron beam X-ray tube, comprising:

an electron gun;

an anode extending a length along an anode trajectory that includes at least a curved segment and comprising a material adapted to emit X-rays upon electrons impinging on the anode;

the anode having a first portion disposed proximal to the electron gun and a second portion distal to the electron gun;

a scan tube attached to the electron gun and enclosing the anode, wherein the anode trajectory defines a region-of-interest ("ROI") external to the scan tube,-; and a collector disposed adjacent to the second portion of the anode and adapted to receive at least a portion of the electrons from the emitter, the collector being electrically isolated from the scan tube and adapted to be connected for measuring the electric charge produced by the received electrons;

a first magnetic assembly comprising one or more first magnets configured to generate a first magnetic field in a first direction to guide the electrons in a trajectory inside the scan tube without impinging on the anode;

a second magnetic assembly comprising a plurality of second magnets, each configured to generate a respective magnetic field in a respective second direction substantially transverse to the first direction, the plurality of second magnets adapted to deflect the electrons from their guided trajectory toward the anode to cause a movement of location where the electrons impinge on a plurality of portions of the anode;

a controller adapted to control the plurality of second magnets to guide the electrons to impinge upon a plurality of portions of the anode to generate X-rays from a plurality of directions relative to the ROI; and an X-ray detector positioned to receive the X-rays from across the ROI.

13. The scanning electron beam X-ray scanner of claim 12, wherein:

the scanner further comprises at least one set of rotational components, including, an x-ray collimator or an x-ray filter, or both, which is rotatable simultaneously with, and is fixed relative to, the sequential movement of the location where the electrons impinge on the anode.

14. The scanning electron beam X-ray scanner of claim 12, wherein X-ray detector is rotatable simultaneously with, and is fixed relative to, the sequential movement of the location where the electrons impinge on the anode.

15. The scanning electron beam X-ray scanner of claim 12, wherein a multiview imaging, a tomosynthesis imaging, a CT imaging, or any combined imaging is used.

16. The scanning Electron Beam X-ray scanner of claim 12, further comprising a magnetic return, wherein the magnets share the magnetic return.

17. The scanning Electron Beam X-ray scanner of claim 12, wherein the controller comprises a power supply and a control circuit, the power supply being adapted provide power to energize a subset, but not the entirety, of the plurality of magnets, the control circuit being adapted to sequentially apply the power provided by the power supply to different subsets of the magnets.

18. A scanning electron beam X-ray scanner of claim 12, comprising:

a scanning electron beam X-ray tube, comprising:

an electron gun;

an anode extending a length along an anode trajectory that includes at least a curved segment and comprising a material adapted to emit X-rays upon electrons impinging on the anode;

the anode having a first portion disposed proximal to the electron gun and a second portion distal to the electron gun; and a scan tube attached to the electron gun and enclosing the anode, wherein the anode trajectory defines a region-of-interest ("ROI") external to the scan tube;

a first magnetic assembly comprising one or more first magnets configured to generate a first magnetic field in a first direction to guide the electrons in a trajectory inside the scan tube without impinging on the anode;

a second magnetic assembly comprising a plurality of second magnets, each configured to generate a respective magnetic field in a respective second direction substantially transverse to the first direction, the plurality of second magnets adapted to deflect the electrons from their guided trajectory toward the anode to cause a movement of location where the electrons impinge on a plurality of portions of the anode;

a controller adapted to control the plurality of second magnets to guide the electrons to impinge upon a plurality of portions of the anode to generate X-rays from a plurality of directions relative to the ROI; and an X-ray detector positioned to receive the X-rays from across the ROI, wherein the generated X-rays are not intercepted by the magnetic assemblies.

* * * * *